US009357914B2

(12) United States Patent
Sakagawa

(10) Patent No.: US 9,357,914 B2
(45) Date of Patent: Jun. 7, 2016

(54) OPHTHALMOLOGIC APPARATUS, METHOD FOR CONTROLLING OPHTHALMOLOGIC APPARATUS, AND STORAGE MEDIUM

(71) Applicant: CANON KABUSHIKI KAISHA, Tokyo (JP)

(72) Inventor: Wataru Sakagawa, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 18 days.

(21) Appl. No.: 13/765,058

(22) Filed: Feb. 12, 2013

(65) Prior Publication Data
US 2013/0208244 A1 Aug. 15, 2013

(30) Foreign Application Priority Data
Feb. 15, 2012 (JP) .................. 2012-030666

(51) Int. Cl.
*A61B 3/10* (2006.01)
*A61B 3/14* (2006.01)
*A61B 3/00* (2006.01)

(52) U.S. Cl.
CPC .................... *A61B 3/0091* (2013.01)

(58) Field of Classification Search
CPC .......... A61B 3/135; A61B 3/103; A61B 3/14; A61B 3/113; A61B 3/1225; A61B 3/024; A61B 3/032; A61B 3/1015

USPC .............. 351/214, 200, 204–206, 209–211, 351/221–223, 246
See application file for complete search history.

(56) References Cited

U.S. PATENT DOCUMENTS

| 5,684,562 A * | 11/1997 | Fujieda .......................... 351/212 |
| 5,751,396 A * | 5/1998 | Masuda et al. ................. 351/221 |
| 8,079,708 B2 * | 12/2011 | Hamaguchi et al. ........... 351/205 |
| 2005/0018132 A1 * | 1/2005 | Fukuma et al. ................ 351/200 |
| 2005/0041210 A1 * | 2/2005 | Isogai et al. ................... 351/205 |
| 2012/0057130 A1 * | 3/2012 | Naito ............................. 351/211 |
| 2012/0188357 A1 * | 7/2012 | Hiramatsu et al. .............. 348/78 |

FOREIGN PATENT DOCUMENTS

| JP | 6233740 A | 8/1994 |
| JP | 4233426 B2 | 3/2009 |
| WO | WO 2010122973 A1 * | 10/2010 |

* cited by examiner

*Primary Examiner* — Dawayne A Pinkney
(74) *Attorney, Agent, or Firm* — Canon USA Inc. IP Division

(57) ABSTRACT

An ophthalmologic apparatus includes an acquisition unit configured to acquire information about a pupil of a subject's eye, and a control change unit configured to change a method of fogging control for moving a fixation target image away from the subject's eye according to the information acquired by the acquisition unit.

10 Claims, 8 Drawing Sheets

OPHTHALMOLOGIC APPARATUS, METHOD FOR CONTROLLING OPHTHALMOLOGIC APPARATUS, AND STORAGE MEDIUM

BACKGROUND OF THE INVENTION

1. Field of the Invention

The present invention relates to an ophthalmologic apparatus, a method for controlling the ophthalmologic apparatus, and a storage medium storing instructions for controlling the ophthalmologic apparatus.

2. Description of the Related Art

A refraction test is an eye exam technique to determine whether a person's eye has a refractive error. Thus, the refraction test enables an ophthalmologist or optometrist to measure a person's prescription for eyeglasses or contact lenses. Fogging is a technique widely used in conventional eye refractive power measurement apparatuses which measure information about refractive power of a subject's eye. Fogging includes projecting a fixation target onto the subject's eye and moving the position of the fixation target image from a reference position based on a result of preliminary measurement to a far side, thereby promoting relaxation of the subject's eye.

If the subject's eye has a high degree of astigmatism, the subject's eye may fail to relax sufficiently. Japanese Patent Application Laid-Open No. 06-233740 discusses a technology for performing feedback control to move the position of the fixation target image in a direction of relaxing the accommodation ability according to measured astigmatism information.

Elderly people may have a pupil diameter of 2 mm or less. To prevent a measurement failure due to shielding of a light flux by the iris, Japanese Patent No. 4233426 discusses a technique for providing a ring-shaped aperture to be conjugate with a small pupil aside from one for a standard pupil.

In order for the subject's eye to be sufficiently relaxed by fogging control, the subject's eye needs to visually identify a change of the image forming position of the fixation target image. If the subject's eye has a small pupil diameter and thus a large depth of focus, a change of the image forming position is less visually identifiable. This has resulted in a problem that the eye having a small pupil diameter fails to be sufficiently relaxed and the eye refractive power measurement ends without a change in measurement.

More specifically, a subject's eye having a standard pupil can visually identify a change of the fixation target image when the fixation target image is moved to a far side. Measurement is successively performed with the subject's eye retaining a less and less accommodation ability, so that the measurement can be ended with no accommodation ability. On the other hand, the eye having a small pupil diameter may fail to visually identify a change of the fixation target image even if the fixation target image is moved to a far side. The accommodation ability remains unchanged, and measurement is successively performed with the accommodation ability still remaining. As a result, the measurement may be ended because there is no change in measurements.

SUMMARY OF THE INVENTION

Certain embodiments of the present invention are directed to an ophthalmologic apparatus capable of making a subject's eye having a nonstandard pupil (a subject's eye having a large depth of focus) visually identify a change of a fixation target image, an ophthalmologic control apparatus, a method for controlling the ophthalmologic apparatus, and a storage medium.

Embodiments of the present invention are also directed to providing operations and effects that are derived from configurations described herein but not obtainable by conventional techniques.

According to an aspect of the present invention, an ophthalmologic apparatus includes an acquisition unit configured to acquire information about a pupil of a subject's eye, and a control change unit configured to change a method of fogging control for moving a fixation target image away from the subject's eye according to the information acquired by the acquisition unit.

According to exemplary embodiments of the present invention, a subject's eye having a nonstandard pupil (a subject's eye having a large depth of focus) can be made to visually identify a change of the fixation target image.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Overall Configuration of Dioptometer

Figure 2:
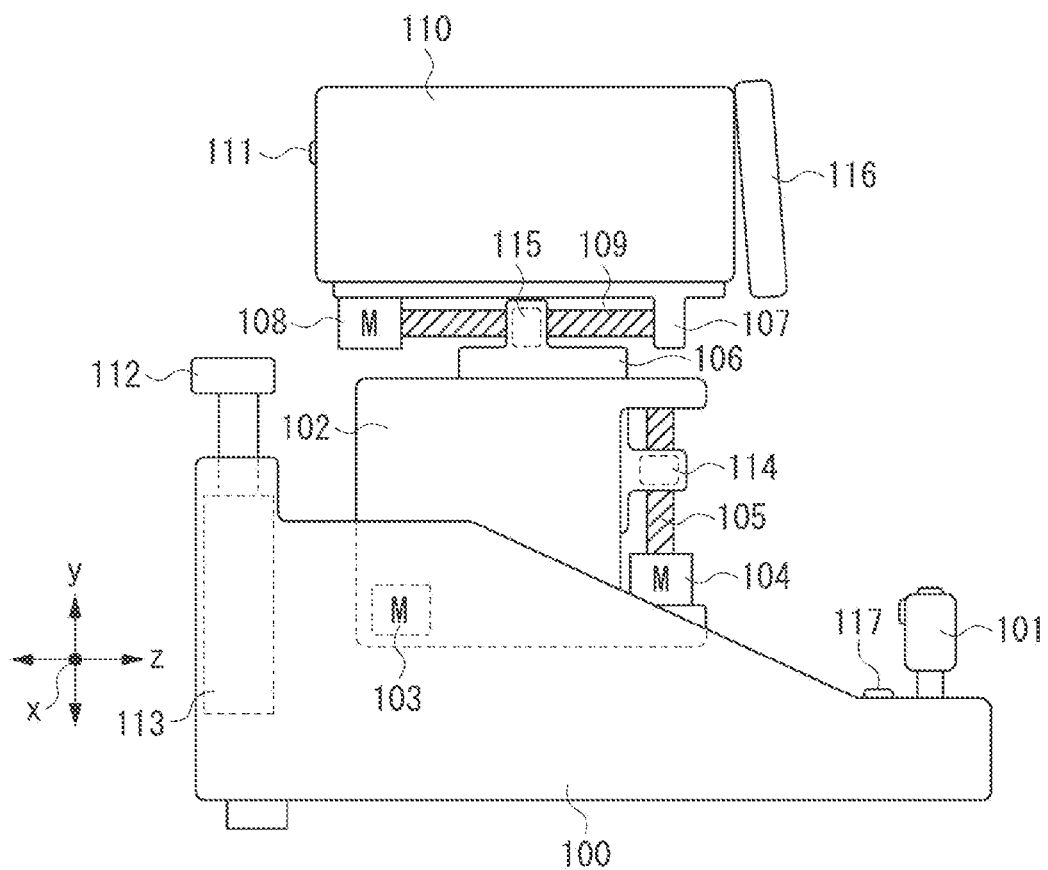
FIG. 2 is an external view of the dioptometer according to the first exemplary embodiment.

A first exemplary embodiment will be described below. FIG. 2 illustrates a schematic overall configuration diagram of a dioptometer of an ophthalmologic apparatus according to the present exemplary embodiment. A frame 102 is movable in a horizontal direction (hereinafter, referred to as an X-axis direction) with respect to a base 100. An X-axis direction drive mechanism includes an X-axis drive motor 103, a feed screw (not illustrated), and a nut (not illustrated). The X-axis drive motor 103 is fixed to the base 100. The feed screw is coupled to an output shaft of the X-axis drive motor 103. The nut can move over the feed screw in the X-axis direction and is fixed to the frame 102. The X-axis drive motor 103 rotates to move the frame 102 in the X-axis direction via the feed screw and the nut. A frame 106 is movable in a vertical direction (hereinafter, a Y-axis direction) with respect to the frame 102.

A Y-axis direction drive mechanism includes a Y-axis drive motor 104, a feed screw 105, and a nut 114. The Y-axis drive motor 104 is fixed to the frame 102. The feed screw 105 is coupled to an output shaft of the Y-axis drive motor 104. The nut 114 can move over the feed screw 105 in the Y-axis direction and is fixed to the frame 106. The Y-axis drive motor 104 rotates to move the frame 106 in the Y-axis direction via the feed screw 105 and the nut 114.

A frame 107 is movable in a front-to-back direction (hereinafter, a Z-axis direction) with respect to the frame 106. A Z-axis direction drive mechanism includes a Z-axis drive motor 108, a feed screw 109, and a nut 115. The Z-axis drive motor 108 is fixed to the frame 107. The feed screw 109 is coupled to an output shaft of the Z-axis drive motor 108. The nut 115 can move over the feed screw 109 in the Z-axis direction and is fixed to the frame 106.

The motor 108 rotates to move the frame 107 in the Z-axis direction via the feed screw 109 and the nut 115. A measurement unit 110 intended for measurement of a subject's eye is fixed to the frame 107. A light source 111 intended for alignment is arranged on a subject-side end of the measurement unit 110. The base 100 includes a joystick 101 for controlling a position of the measurement unit 110 and an eye refractive power measurement diaphragm switching key 117 for switching eye refractive power measurement diaphragms to be described below.

For eye refractive power measurement, a patient (subject) places his/her chin on a chin rest 112 and presses his/her forehead against a forehead rest portion of a frame of a face rest (not illustrated) fixed to the base 100. In this manner, the position of the subject's eye may be accurately fixed in a measurement position. The chin rest 112 can be adjusted in the Y-axis direction according to the size of the subject's face by using a chin rest drive mechanism 113. A liquid crystal display (LCD) monitor 116, which is a display device for observing the subject's eye E, is arranged on an examiner-side end of the measurement unit 110. The LCD monitor 116 can display measurement results and other information.

Eye Refractive Power Measurement System

Figure 1:
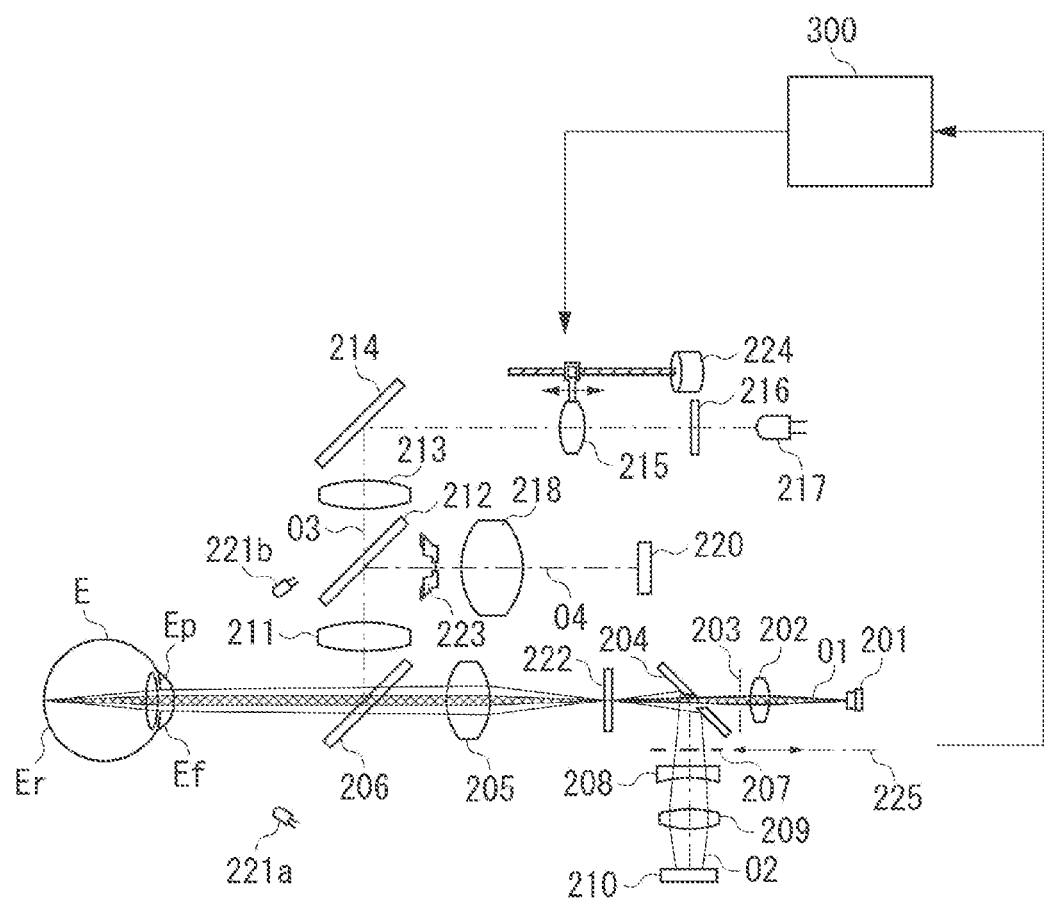
FIG. 1 is a layout diagram illustrating optical systems for eye refractive power measurement of a dioptometer according to a first exemplary embodiment of the present invention.

FIG. 1 is a layout diagram illustrating optical systems inside the measurement unit 110 (shown in FIG. 2). An eye refractive power measurement light source 201 emits light having a predetermined wavelength (e.g., 880 nm). An optical path 01 extends from the eye refractive power measurement light source 201 to the subject's eye E. A les 202, a diaphragm 203, a perforated mirror 204, an insertable and removable diffusion plate 222, and a lens 205 are arranged on the optical path 01. The diaphragm 203 is generally disposed at a plane conjugate with the pupil Ep of the subject's eye E. A dichroic mirror 206 is further arranged on the optical path 01. The dichroic mirror 206 totally reflects visible light from the side of the subject's eye E and partly reflects the light flux having a wavelength of 880 nm. An eye refractive power measurement diaphragm 207, a light flux spectral prism 208, a lens 209, and an image sensor 210 are arranged in succession on an optical path 02 which extends in a reflecting direction of the perforated mirror 204.

Eye refractive power measurement diaphragms to be positioned generally conjugate with the pupil Ep include a standard pupil diameter diaphragm 207 and a small pupil diameter diaphragm 225. Either one of the diaphragms 207 and 225 is always placed on the optical path 02 by an eye refractive power measurement diaphragm switching solenoid (not illustrated). As used herein, a standard pupil diameter (a normal pupil diameter) refers to a standard pupil diameter of a standard subject's eye (for example, a pupil diameter greater than 4 mm or greater than 3.3 mm). The standard pupil diameter diaphragm 207 refers to a diaphragm that is suited to the standard pupil diameter of the standard subject's eye.

A small pupil diameter refers to a pupil diameter (i.e., a pupil diameter smaller than 4 mm or smaller than 3.3 mm) smaller than the standard pupil diameter. The small pupil diameter diaphragm 225 refers to a diaphragm that is suited to the small pupil diameter. It should be noted that pupil diameters determined to be small pupil diameters are not limited to ones smaller than 4 mm or smaller than 3.3 mm. Pupil diameters smaller than other values may be determined to be small pupil diameters.

During eye refractive power measurement, the semi-transparent diffusion plate 222 is positioned out of the optical path 01 by a not-illustrated diffusion plate insertion and removal solenoid. The eye refractive power measurement light source 201 emits a light flux. The diaphragm 203 narrows the light flux onto the optical path 01. The lens 202 forms a primary image of the light flux in front of the lens 205. The light flux is transmitted through the lens 205 and the dichroic mirror 206 and projected onto the pupil center of the subject's eye E.

The light flux forms an image on the fundus Er of the subject's eye E, and the reflected light passes through the pupil center and is made incident on the lens 205 again. The incident light flux is transmitted through the lens 205 and then reflected by the periphery of the perforated mirror 204. The reflected light reflux is pupil-separated by the standard pupil diameter diaphragm 207 or the small pupil diameter diaphragm 225 generally conjugate with the pupil Ep of the subject's eye E. The standard pupil diameter diaphragm 207 and the small pupil diameter diaphragm 225 both have a ring-shaped slit. The pupil-separated light flux is projected onto a light receiving surface of the image sensor 210 as a ring image.

If the subject's eye E is an emmetropic (well proportioned) eye, the ring image forms as a predetermined circle. If the subject's eye E is a myopic eye, the ring image forms as a circle smaller than that of an emmetropic eye. If the subject's eye E is a hypermetropic eye, the ring image forms a circle greater than that of an emmetropic eye. If the subject's eye E is astigmatic, the ring image forms an ellipse. The angle formed between the horizontal axis and the major or minor axis of the ellipse is an astigmatic axis angle. Eye refractive power is determined based on the coefficient (ellipticity) of the ellipse.

Now, a fixation target projection optical system and an alignment light receiving optical system are arranged in a reflecting direction of the dichroic mirror 206. The alignment light receiving optical system is used both for observation of the anterior segment of the subject's eye E and for alignment detection. A lens 211, a dichroic mirror 212, a lens 213, a folding mirror 214, a lens 215, a fixation target 216, and a fixation target illumination light source 217 are arranged in succession on an optical path 03 of the fixation target projection optical system.

For fixation guiding, the fixation target illumination light source 217 is lit to illuminate the fixation target 216 with a projection light flux from behind. The projection light flux is projected onto the fundus Er of the subject's eye E through the lens 215, the folding mirror 214, the lens 213, the dichroic mirror 212, and the lens 211. To achieve a fogging state of the subject's eye E, the lens 215 is configured to be movable to a far side in the direction of the optical axis by a fixation guiding motor 224, which performs diopter guiding control.

An optical path 04 extends in a reflecting direction of the dichroic mirror 212. An alignment prism diaphragm 223, a lens 218, and an image sensor 220 are arranged in succession on the optical path 04. Anterior segment illumination light sources 221a and 221b are arranged near a measurement section of the ophthalmologic apparatus. The anterior segment illumination light sources 221a and 221b are light sources for illuminating the anterior segment of the subject's eye E, and have a wavelength of around 780 nm. A light flux of an anterior segment image of the subject's eye E illuminated by the anterior segment illumination light sources 221a and 221b passes through the optical path 04 and forms an image on the image sensor 220.

Figure 4:
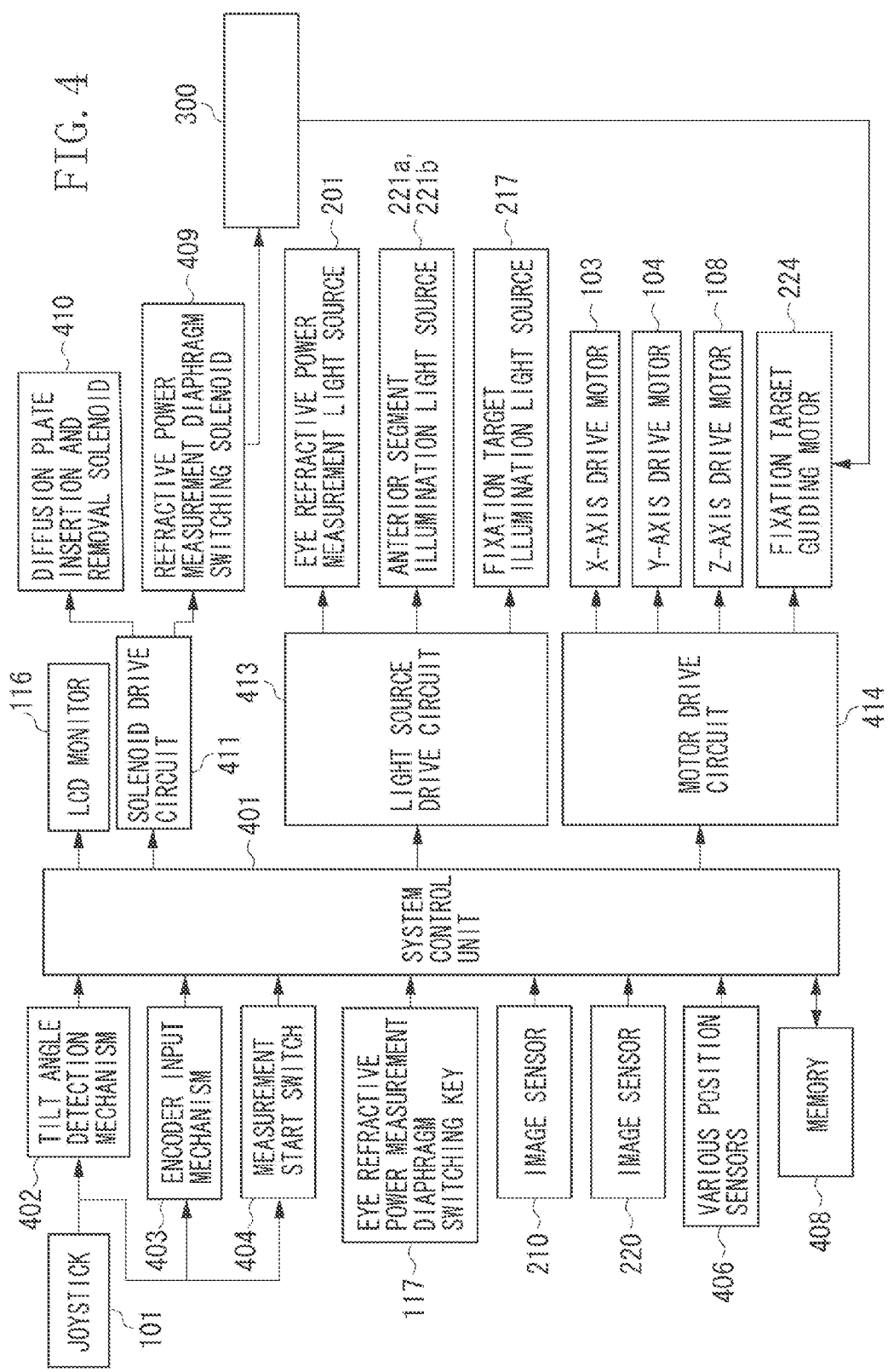
FIG. 4 is a system block diagram of the dioptometer according to the first exemplary embodiment.

For alignment, the diffusion plate 222 is inserted into the optical path 01 by a diffusion plate insertion and removal solenoid 410 (illustrated in FIG. 4). The foregoing eye refractive power measurement light source 201 is also used as a light source for alignment detection. The diffusion plate 222 is inserted into a position where a primary image of the eye refractive power measurement light source 201 is formed by the projection lens 202. The position coincides with a focal position of the lens 205. Consequently, an image of the eye refractive power measurement light source 201 is formed on the diffusion plate 222 once, and the image serves as a secondary light source to project a wide parallel light flux onto the subject's eye E through the lens 205.

The parallel light flux is reflected by the cornea Ef of the subject's eye E. The reflected light flux is spectrally dispersed through the alignment prism diaphragm 223 and converged on the image sensor 220 through the lens 218. Since the image formed on the image sensor 220 has a luminescent spot in a different position depending on the position of the subject's eye E, the subject's eye E can be aligned based on the position of the luminescent spot.

A fogging control change unit 300 will be described in detail below.

Measurement Diaphragm Aperture

Figure 3:
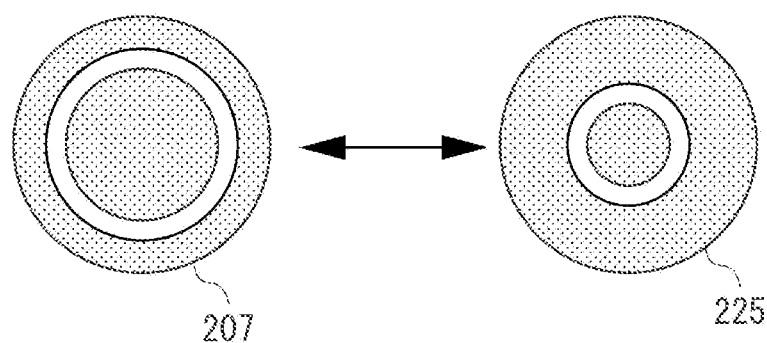
FIG. 3 is a comparison diagram illustrating two types of eye refractive power measurement diaphragms related to pupil diameters.

FIG. 3 illustrates the shapes of two types of eye refractive power measurement diaphragm apertures (ring-shaped openings). The small pupil diameter diaphragm 225 has a ring-shaped slit (a ring-shaped opening) smaller than that of the standard pupil diameter diaphragm 207 in radius (diameter). The small pupil diameter diaphragm 225 can thus separate a light flux that passes a closer portion to the cornea center. Portions closer to the cornea center have lower refractive power and are not optimum for eye refractive power measurement. However, such portions are less likely to be shielded by the iris and are suited to the measurement of a subject's eye E having a small pupil diameter. In FIG. 3, the small pupil diameter diaphragm 225 has an opening (a slit) smaller than that of the standard pupil diameter diaphragm 207 in inner and outer diameters. This is not restrictive. For example, only the inner diameter of the opening may be smaller.

When the examiner operates the eye refractive power measurement diaphragm switching key 117, the standard pupil diameter diaphragm 207 is switched to the small pupil diameter diaphragm 225 if the standard pupil diameter diaphragm 207 has been placed in the optical path 02 before the operation. According to the switching, the fogging control change unit 300 changes control of the movement of a fixation target image with respect to the subject's eye E. Such operations will also be described in detail below. Alternatively, a computer may calculate the pupil diameter of the subject's eye E to automatically switch between the standard pupil diameter diaphragm 207 and the small pupil diameter diaphragm 225 according to the pupil diameter.

System Control

FIG. 4 is a system block diagram illustrating the dioptometer according to the present exemplary embodiment. A system control unit 401 controls the entire system. The system control unit 401 includes a program storage unit, a data storage unit, an input/output control unit, and an arithmetic processing unit. The data storage unit stores data for correcting eye refractive power values. The input/output control unit controls various device inputs and outputs. The arithmetic processing unit calculates data obtained from various devices. A control at the start of test, an automatic alignment control, an eye refractive power measurement control, and a fogging control will be described below with reference to FIG. 4.

1) Control at the Start of Test

At the start of test, the system control unit 401 initially turns on the eye refractive power measurement light source 201, the anterior segment illumination light sources 221a and 221b, and the fixation target illumination light source 217 via a light source drive circuit 413. The examiner operates the joystick 101 to position the measurement unit 110 to the subject's eye E. A tilt angle detection mechanism 402, an encoder input mechanism 403, and a measurement start switch 404 are arranged on the joystick 101. The tilt angle detection mechanism 402 is intended to detect a tilt in front, back, right, and left directions. The encoder input mechanism 404 is intended to detect rotation. The measurement start switch 404 is pressed to start measurement.

According to inputs from the tilt angle detection mechanism 402 and the encoder input mechanism 403, the system control unit 401 drives the X-axis drive motor 103, the Y-axis drive motor 104, and the Z-axis drive motor 108 via a motor drive circuit 414 to control the position of the measurement unit 110. At the same time, the system control unit 401 synthesizes an anterior segment image of the subject's eye E captured by the image sensor 220 and character and graphic data, and displays the resultant on the LCD monitor 116.

The examiner observes the anterior segment of the subject's eye E displayed on the LCD monitor 116. If the pupil diameter is determined to be insufficient, the examiner presses the eye refractive power measurement diaphragm switching key 117. The system control unit 401 then operates a refractive power measurement diaphragm switching solenoid 409 to switch between the standard pupil diameter diaphragm 207 and the small pupil diameter diaphragm 225. Since the refractive power measurement diaphragm switching solenoid 409 changes its position depending on which of the standard pupil diameter diaphragm 207 and the small pupil diameter diaphragm 225 is in the optical path 02, the refractive power measurement diaphragm switching solenoid 409 functions as an acquisition unit for acquiring information about the pupil Ep of the subject's eye E.

2) Automatic Alignment Control

When the examiner presses the measurement start switch 404, the system control unit 401 starts the automatic alignment control. In the automatic alignment control, the system control unit 401 analyzes the anterior segment image obtained by the image sensor 220 to detect the pupil Ep of the subject's eye E. When the pupil Ep is detected, the system control unit 401 performs X- and Y-axis motor control via the motor drive circuit 414 in directions such that the center axis of the pupil Ep coincides with the optical axis of the measurement unit 110.

When the center axis of the pupil Ep of the subject's eye E generally coincides with the optical axis of the measurement unit 110, reflection of the light from the anterior segment illumination light source 221a and reflection of the light from the anterior segment illumination light source 221b appear on the anterior segment. The system control unit 401 performs X-, Y-, and Z-axis motor control so that the reflections come to a predetermined position and size. The system control unit 401 detects a luminescent spot spectrally dispersed by the alignment prism diaphragm 223, and controls the motor drive circuit 414 according to the position of the luminescent spot. The system control unit 401 then performs X-, Y-, and Z-axis fine motor control. If the position of the luminescent spot falls within a predetermined range, the system control unit 401 completes the automatic alignment control and proceeds to eye refractive power measurement.

3) Eye Refractive Power Measurement Control

At the time of eye refractive power measurement, the system control unit 401 retracts the diffusion plate 222, which has been inserted in the optical path 01 for the automatic alignment control, from the optical path 01. The system control unit 401 adjusts the amount of the light from the eye refractive power measurement light source 201 to project a measurement light flux onto the fundus Er of the subject's eye E. Reflected light from the fundus Er travels through the optical path 02 and is received by the image sensor 210. The image sensor 210 captures the reflected light from the fundus Er as a ring-shaped image through the standard pupil diameter diaphragm 207 or the small pupil diameter diaphragm 225. The ring image is stored in a memory 408.

The system control unit 401 calculates the barycentric coordinates of the ring image stored in the memory 408, and determines an ellipse equation by a known method. The system control unit 401 calculates the major and minor diameters of the determined ellipse and the tilt of the major axis to calculate eye refractive power of the subject's eye E, and displays the eye refractive power on the LCD monitor 116. Eye refractive power values corresponding to the major and minor diameters of the determined ellipse and a relationship between the angles of the elliptic axes and the astigmatic axis on the light receiving surface of the image sensor 210 are corrected in advance in a manufacturing process of the ophthalmologic apparatus.

4) Fogging Control

In the fogging control, the motor drive circuit 414 drives the lens 215 by using the fixation guiding motor 224, whereby the fixation target image is moved to a position corresponding to an eye refractive power value determined by preliminary measurement. Consequently, the fixation target image is formed on the fundus Er of the subject's eye E. The system control unit 401 then moves the lens 215 further to a far side by a predetermined amount to fog the fixation target 216. The fixation target image is formed slightly in front of the fundus Er of the subject's eye E. The subject's eye E is adjusted to be focused on a far side to form a fixation target image.

The adjustment relaxes the subject's eye E. In the present exemplary embodiment, the lens 215 is moved to achieve fogging. In another exemplary embodiment, the lens 215 may be fixed while the fixation target 216 is moved for fogging. The lens 215 and the fixation target 216 both may be moved. The system control unit 401 repeats such a fogging control and the measurement of an eye refractive power value until an end condition to be described below is satisfied. As a result, an eye refractive power value can be obtained with the subject's eye E sufficiently relaxed.

Subject's Eye Having Small Pupil Diameter

In order for the subject's eye E to be sufficiently relaxed, the subject's eye E needs to visually identify a change of the image forming position caused by the fogging control. A subject's eye E having a small pupil has a large depth of focus (a second depth of focus greater than a first depth of focus, where the first depth of focus refers to that of a subject's eye E having a standard pupil diameter), and a change of the image forming position is less visually identifiable. Such a difference will be described with reference to FIGS. 5A, 5B, 5C, and 5D.

Figure 5A:
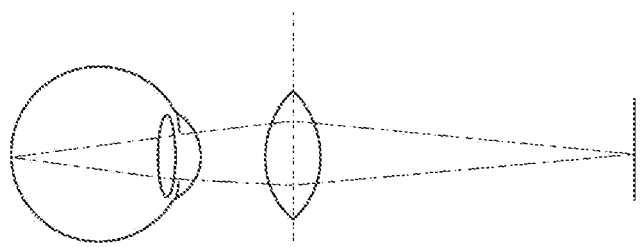
FIGS. 5A, 5B, 5C, and 5D are diagrams illustrating a relationship between the pupil diameter and a depth of focus.
Figure 5B:
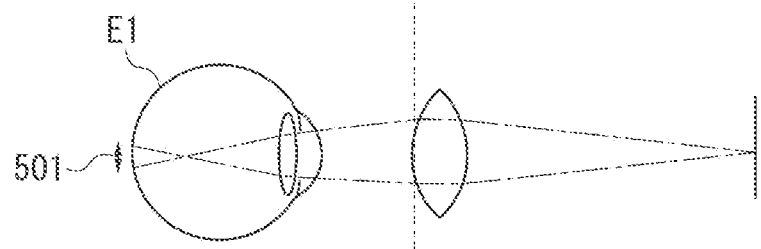

FIG. 5A illustrates a state where a fixation target image is formed on the fundus. Components other than subject's eyes E1 and E2, the lens 215, and the fixation target 216 are omitted. When the lens 215 is moved to the position illustrated in FIG. 5B, a point that has no dimension on the fixation target image is projected on the fundus with a dimension 501. The subject's eye E1 having a standard pupil diameter visually identifies the change of the image forming position.

Figure 5C:
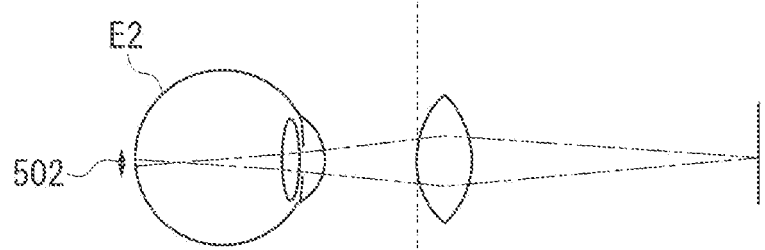
Figure 5D:
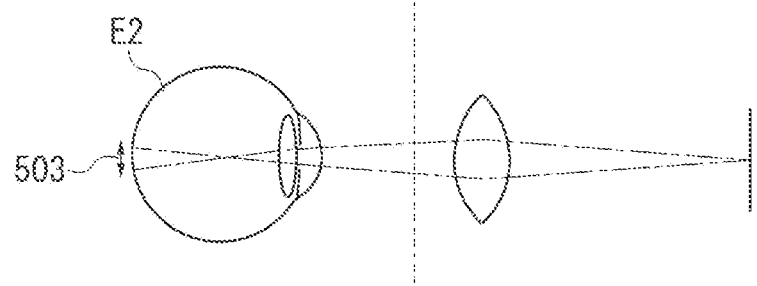

FIG. 5C illustrates the subject's eye E2 having a small pupil diameter. Even if the lens 215 moves to the same position as in FIG. 5B, the projected point has a smaller dimension 502 and the change of the image forming position is less visually identifiable. To project the point on the fundus of the subject's eye E2 with the similar dimension as in FIG. 5B, the lens 215 needs to be moved by a greater amount as illustrated in FIG. 5D. In the present exemplary embodiment, the system control unit 401 determines whether the subject's eye E has a standard pupil diameter or a small pupil diameter. If the subject's eye E has a small pupil diameter, the fogging control change unit 300 (FIGS. 1 and 4) operates to switch the fogging control for a standard pupil diameter to that for a small pupil diameter.

Flow Process of Present Exemplary Embodiment

Figure 6:
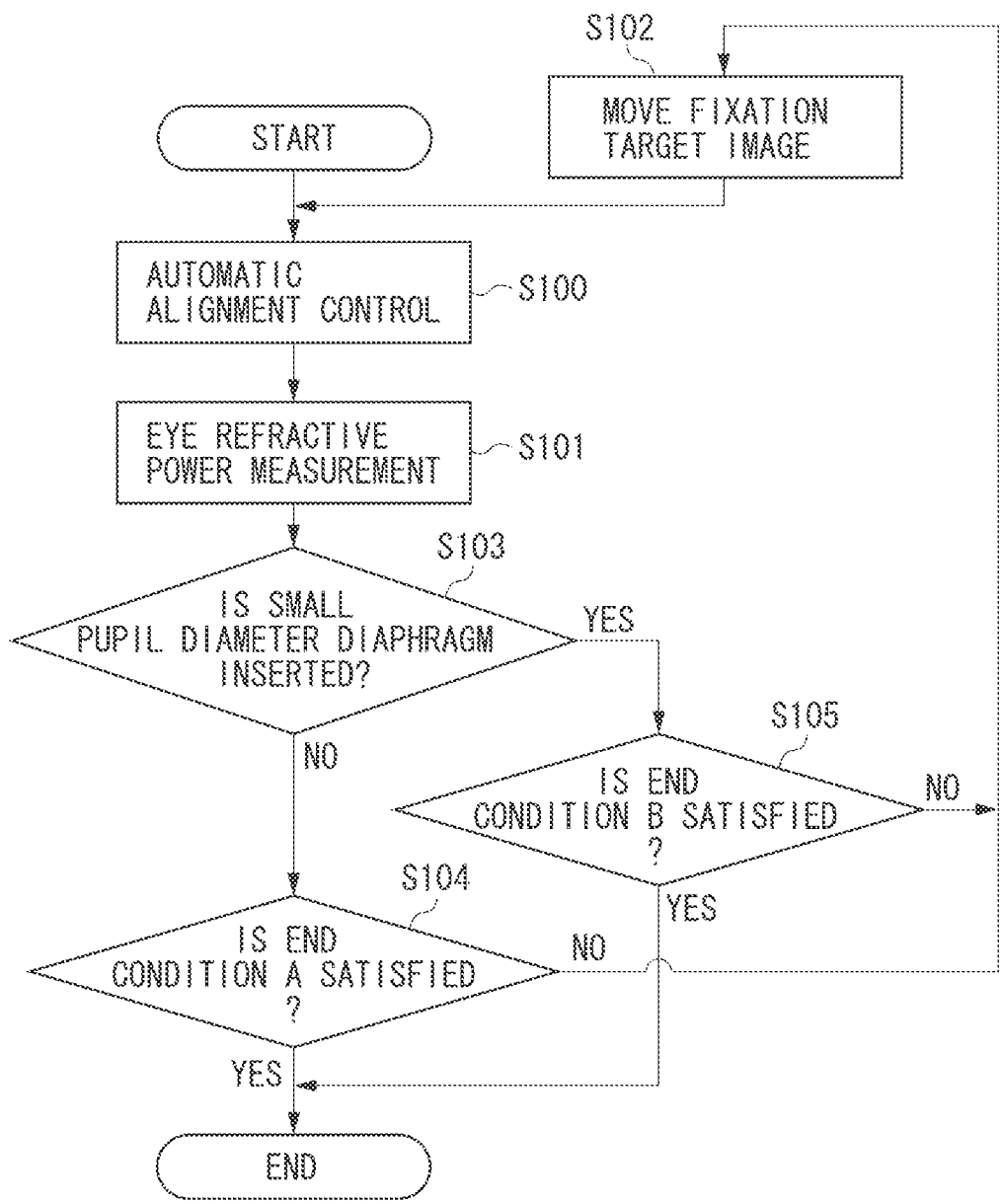
FIG. 6 is a flowchart according to the first exemplary embodiment.

FIG. 6 illustrates an exemplary flow process for eye refractive power measurement of the present exemplary embodiment. The examiner inserts the standard pupil diameter diaphragm 207 or the small pupil diameter diaphragm 225 into the optical path 02 in advance according to the pupil diameter of the subject's eye E. The examiner then presses the measurement start switch 404 to start the flow. When the measurement start switch 404 is pressed, in steps S100 and S101, the system control unit 401 performs the foregoing automatic alignment control and eye refractive power measurement, respectively, in succession. After the end of the eye refractive power measurement, then in step S103, the system control unit 401 determines whether the eye refractive power measurement diaphragm inserted in advance is the standard pupil diameter diaphragm 207 or the small pupil diameter diaphragm 225.

In steps S104 and S105, the system control unit 401 determines whether an end condition set for the respective eye refractive power measurement diaphragms is satisfied. If the end condition is satisfied (there is hardly any change in measurements; YES in step S104 or S105), the system control unit 401 ends the measurement. If the end condition is not satisfied (there is a change in measurements; NO in step S104 or S105), then in step S102, the system control unit 401 moves the fixation target image. Such is the flow of the present exemplary embodiment. For example, the end condition A of step S104 and the end condition B of step S105 may be determined as follows. The end condition A is such that eye refractive power has been measured twice or more (the fixation target image has been moved twice or more) and a difference between the last two measurements is smaller than or equal to 0.25 diopters (D).

The end condition B is such that eye refractive power has been measured three times or more (the fixation target image has been moved three times or more) and a difference between maximum and minimum measurements among the last three measurements is smaller than or equal to 0.25 D. Typically, fogging can be repeated to sufficiently relax the subject's eye E to reduce a change in the eye refractive power measurements. Since further fogging without a change increases the test time, the test can be ended when there is no more changes. Under the end condition A, the subject's eye E is thus determined to be sufficiently relaxed if a difference between the measurements at the last two moves of the fixation target image is small.

On the other hand, if the subject's eye E has a small pupil diameter, the subject's eye E may fail to visually identify an enough change of the image forming position of the fixation target image caused by fogging and fail to be sufficiently relaxed. Under the end condition B, the system control unit 401 therefore performs fogging again even if a difference between the last two measurements is small, and compares the measurements at the last three moves of the fixation target image.

As described above, the system control unit 401 switches the end conditions, or equivalently, changes control of the movement of the fixation target image with respect to the subject's eye E according to the inserted eye refractive power measurement diaphragm. The ophthalmologic apparatus can thus achieve both a reduced test time and accurate measurements. The number of times of measurement is not limited to the foregoing two and three. The number of times of measurement under the end condition B has only to be greater than that under the end condition A.

Figure 7:
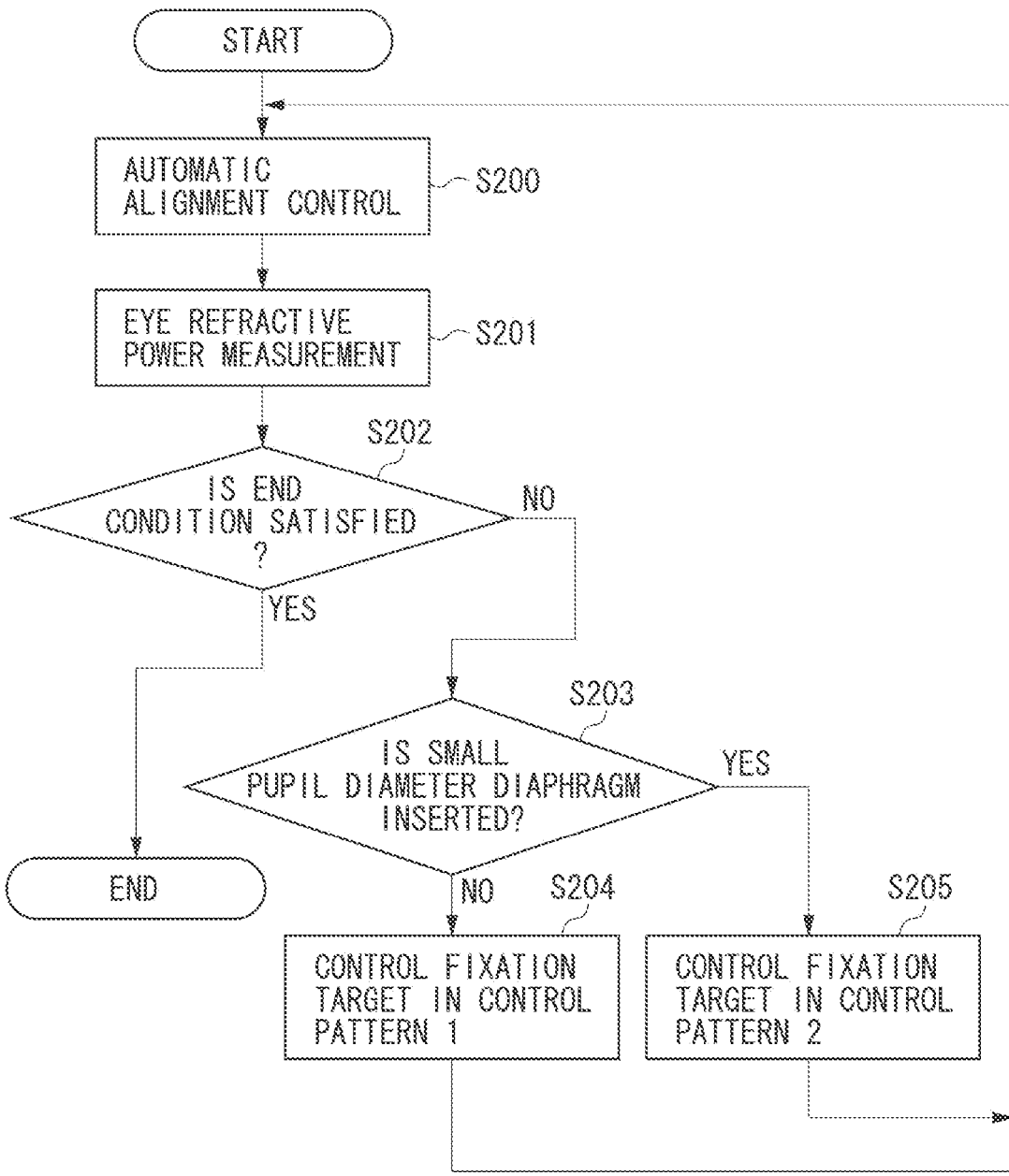
FIG. 7 is a flowchart according to a second exemplary embodiment.

A second exemplary embodiment will be described below. The present exemplary embodiment is similar to the first exemplary embodiment in the configuration of the ophthalmologic apparatus, and different only in the flow. FIG. 7 illustrates the exemplary flow according to the present exemplary embodiment. The examiner inserts the standard pupil diameter diaphragm 207 or the small pupil diameter diaphragm 225 in advance according to the pupil diameter of the subject's eye E. The examiner presses the measurement start switch 404 to start the flow. In steps S200 and S201, the system control unit 401 performs the automatic alignment control and eye refractive power measurement in a manner similar to steps S100 and S101 of the first exemplary embodiment. The end condition of step S202 is similar to the end condition A according to the first exemplary embodiment.

More specifically, the end condition is such that eye refractive power has been measured twice or more and a difference between the last two measurements is smaller than or equal to 0.25 D. If the end condition is satisfied (YES in step S202), the system control unit 401 ends the test. If the end condition is not satisfied (NO in step S202), then in step S203, the system control unit 401 determines the eye refractive power measurement diaphragm. If the standard pupil diameter diaphragm 207 is inserted (NO in step S203), then in step S204, the system control unit 401 controls the fixation target 216 in a control pattern 1. If the small pupil diameter diaphragm 225 is inserted (YES in step S203), then in step S205, the system control unit 401 controls the fixation target 216 in a control pattern 2. For example, the control patterns 1 and 2 can be as follows:

The control pattern 1 includes control to move the fixation target 216 from the current position to a far position at a moving distance equivalent to 0.75 D. The control pattern 2 includes control to move the fixation target 216 from the current position to a far position at a moving distance equivalent to 1 D (a farther position than that in the control pattern 1). Such switching of the control patterns 1 and 2 according to the inserted eye refractive power measurement diaphragm can achieve both a reduced test time and accurate measurements. The foregoing moving distances are not limited to the distances equivalent to 0.75 D and 1 D. The moving distance of the control pattern 2 has only to be greater than that of the control pattern 1.

Figure 8:
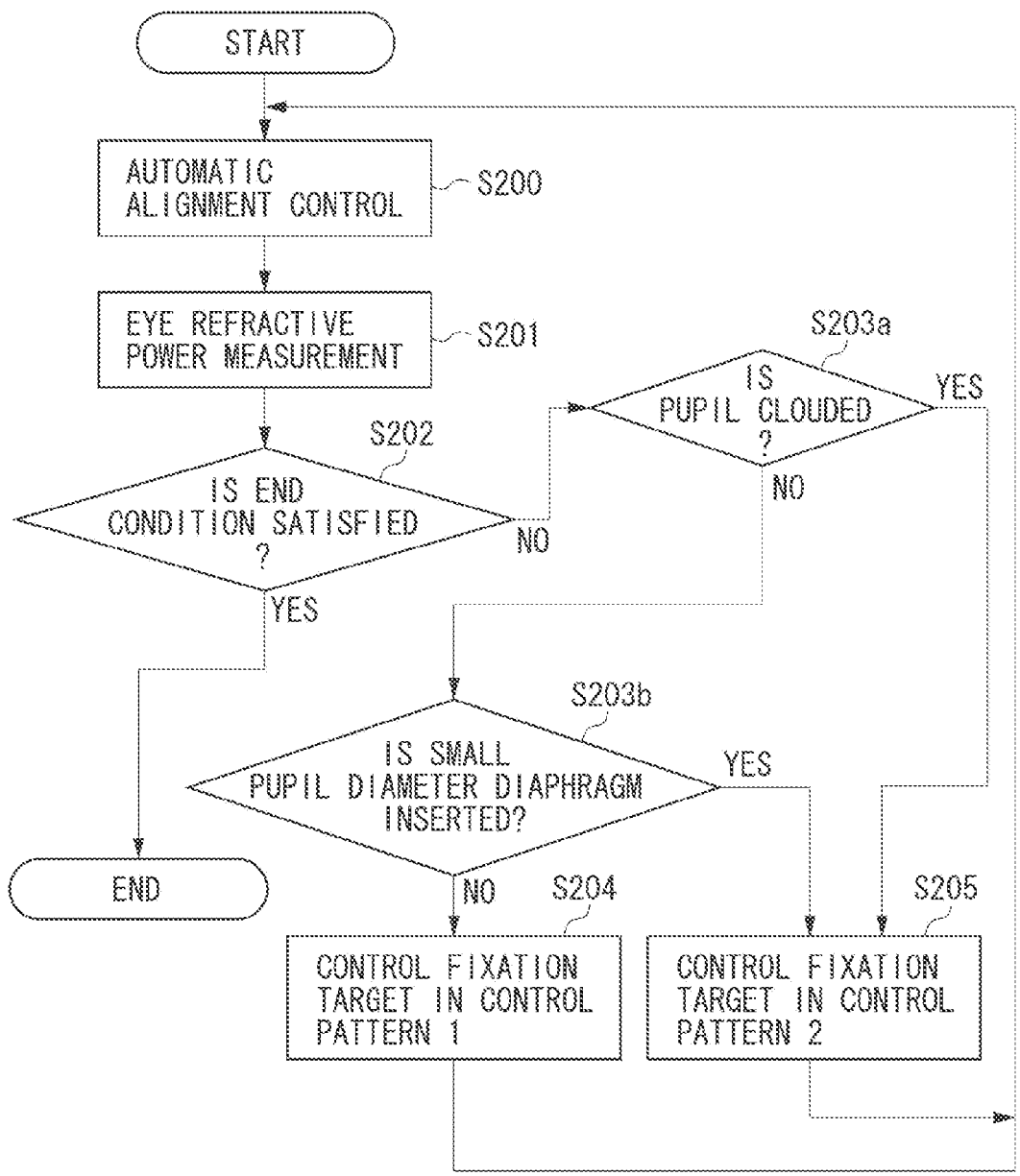
FIG. 8 is a flowchart according to a third exemplary embodiment.

A third exemplary embodiment will be described below. FIG. 8 illustrates a flow of the present exemplary embodiment, which is similar to that of the second exemplary embodiment and includes additional step S203a (a step of, if the end condition is not satisfied, determining whether the pupil Ep includes a predetermined amount of clouding or more). A threshold whether the pupil Ep includes a predetermined amount of clouding or more may be any appropriate value that relates to the number of spots where a cloud, large or small, is observed, the number of spots where a cloud having a predetermined area or more is observed, and/or the area ratio of clouding to the pupil Ep.

Step S203b of FIG. 8 corresponds to step S203 of FIG. 7. Similar steps to those of FIG. 7 are designated by the same reference numerals. If the end condition is not satisfied (NO in step S202) and the pupil Ep includes a predetermined amount of clouding or more (YES in step S203a), then in step S205, the system control unit 401 controls the fixation target 216 in the control pattern 2 in the same manner when the small pupil diameter diaphragm 225 is inserted.

In the flow in FIG. 8, step S203b is performed after step S203a. This is not restrictive, and step S203a may be performed after step S203b.

The foregoing exemplary embodiments use the two types of control patterns concerning the movement of the fixation target image with respect to the subject's eye E. However, the number of types of control patterns need not be two and may be three or more. If there are three or more types of eye refractive power measurement diaphragms corresponding to depths of focus of the subject's eye E, or if the aperture area of an eye refractive power measurement diaphragm changes continuously, three or more types of control patterns concerning the movement of the fixation target image with respect to the subject's eye E can be provided. Alternatively, a control pattern can be changed in a continuous manner.

The information about the pupil Ep of the subject's eye E equivalent to information about the depth of focus need not be information about the inserted eye refractive power measurement diaphragm, or, more specifically, information about the size or area of the diaphragm aperture arranged to be optically conjugate with the pupil Ep of the subject's eye E. For example, the system control unit 401 may measure the pupil diameter of the subject's eye E as information about the size of the pupil Ep of the subject's eye E. Information about the clouding state of the pupil Ep of the subject's eye E and/or the subject's age may be used. In other words, the system control unit 401 may acquire information about the clouding state of the pupil Ep of the subject's eye E (if clouding has progressed beyond the clouding state of the pupil Ep of a standard subject's eye E, the depth of focus becomes greater as with an eye having a small pupil diameter).

Alternatively, the system control unit 401 may acquire information about the subject's age associated with the size of the pupil Ep of the subject's eye E (elderly people may have eyes having a small pupil diameter). For example, the fogging control change unit 300 may operate if the age is 70 or over, or the date of birth is before Jan. 1, 1941.

The system control unit 401 may use any two of the following pieces of information: the size of the pupil Ep of the subject's eye E; the size or area of the diaphragm aperture arranged to be optically conjugate with the pupil Ep of the subject's eye E; the clouding state of the pupil Ep of the subject's eye E; and the subject's age. In such a case, the fogging control change unit 300 may operate if either one of the two pieces of information has a value not satisfying a condition for the fogging control change unit 300 to operate and the other has a value satisfying a condition for the fogging control change unit 300 to operate (steps S203a and S203b of FIG. 8).

Such information may be automatically acquired inside the main body of the ophthalmologic apparatus. The examiner or the subject may input the information into the main body of the ophthalmologic apparatus via an input unit. In an example of the former case, the refractive power measurement diaphragm switching solenoid 409 described in the exemplary embodiments may be used. More specifically, the refractive power measurement switching solenoid 409 changes its position depending on which of the standard pupil diameter diaphragm 207 and the small pupil diameter diaphragm 225 is in the optical path 02, and thus functions as an acquisition unit for acquiring information about the pupil Ep of the subject's eye E. However, an exemplary embodiment of the present invention is not limited thereto, and may use any acquisition unit that can acquire the foregoing information.

In the foregoing exemplary embodiments, a ring-shaped aperture serving as a diaphragm aperture optically conjugate with the pupil Ep of the subject's eye E is arranged in the optical path 02 for receiving the light flux reflected by the fundus Er. However, the ring-shaped aperture may be arranged in the optical path 01 for projecting light onto the fundus Er. The diaphragm aperture is not limited to a ring-shaped aperture, and may be spot-shaped apertures in three longitudinal directions (more preferably, five longitudinal directions which allow identification of a general elliptic shape).

The foregoing exemplary embodiments are applied to a dioptometer which measures the eye refractive power of the subject's eye E. However, the exemplary embodiments of the present invention are not limited thereto, and may be applied to an apparatus that captures a tomographic image of the fundus Er or anterior segment of the subject's eye E. Since the subject's eye E can be relaxed before capturing a tomographic image of the anterior segment, the tomographic image of the anterior segment including the crystalline lens can be captured with less effect of the accommodation ability of the subject's eye E.

In the foregoing exemplary embodiments, the acquisition unit for acquiring information about the pupil Ep of the subject's eye E and the fogging control change unit 300 for changing control of the movement of the fixation target image with respect to the subject's eye E according to the information acquired by the acquisition unit are described to be included in the main body of the ophthalmologic apparatus. However, an exemplary embodiment of the present invention is not limited thereto. The fixation target 216 may be included in the main body of the ophthalmologic apparatus while an ophthalmologic control apparatus including the acquisition unit for acquiring information about the pupil Ep of the subject's eye E and the fogging control change unit 300 for changing control of the movement of the fixation target image with respect to the subject's eye E according to the information acquired by the acquisition unit may be arranged outside the main body of the ophthalmologic apparatus.

Aspects of the present invention can also be realized by a computer of a system or apparatus (or devices such as a CPU or MPU) that reads out and executes a program recorded on a memory device to perform the functions of the above-described embodiment (s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2012-030666 filed Feb. 15, 2012, which is hereby incorporated by reference herein in its entirety.

What is claimed is:

1. An ophthalmologic apparatus comprising:
an acquisition unit configured to acquire information about a pupil of a subject's eye; and
a control change unit configured to change a method of fogging control for moving a fixation target image away from the subject's eye according to the information acquired by the acquisition unit
wherein the control change unit is configured to change a moving a distance or a number of times of movement of the fixation target image according to the information about the pupil acquired by the acquisition unit,
wherein the control change unit is configured, if the information about the pupil indicates a second depth of focus greater than a first depth of focus, to increase the moving distance of the fixation target image or the number of times of movement of the fixation target image as compared to the moving distance or the number of times of movement of the fixation target image when the information about the pupil indicates the first depth of focus.

2. The ophthalmologic apparatus according to claim 1,
wherein the information about the pupil includes information about a size or area of a diaphragm aperture arranged to be optically conjugate with the pupil of the subject's eye, and
wherein the control change unit is configured to operate if the size of the diaphragm aperture is smaller than a predetermined value or if the area of the diaphragm aperture is smaller than a predetermined value.

3. The ophthalmologic apparatus according to claim 1,
wherein the information about the pupil includes information about a clouding state of the pupil of the subject's eye, and
wherein the control change unit is configured to operate if the clouding state of the pupil of the subject's eye includes clouding more than a predetermined clouding state.

4. The ophthalmologic apparatus according to claim 1, wherein the information includes information about a subject's age associated with a size of the pupil of the subject's eye, and
wherein the control change unit is configured to operate if the subject's age exceeds a predetermined age.

5. The ophthalmologic apparatus according to claim 1, wherein the information includes two of a size of the pupil of the subject's eye, a size or area of a diaphragm aperture arranged to be optically conjugate with the pupil of the subject's eye, a clouding state of the pupil of the subject's eye, and a subject's age, and
wherein the control change unit is configured to operate if one of the two has a value not satisfying a condition for the control change unit to operate and the other has a value satisfying a condition for the control change unit to operate.

6. The ophthalmologic apparatus according to claim 1, further comprising a measurement unit configured to measure eye refractive power of the subject's eye by projecting a light flux onto a fundus of the subject's eye to receive the light flux reflected by the fundus.

7. The ophthalmologic apparatus according to claim 6, further comprising a ring-shaped diaphragm aperture in a position optically conjugate with the pupil of the subject's eye in an optical path for receiving the light flux reflected by the fundus.

8. The ophthalmologic apparatus according to claim 1, wherein
the information about the pupil includes information about a size of the pupil of the subject's eye.

9. A method for controlling an ophthalmologic apparatus, the method comprising:
acquiring information about a pupil of a subject's eye;
changing a method of fogging control for moving a fixation target image away from the subject's eye according to the acquired information about the pupil;
changing a moving distance or a number of times of movement of the fixation target image according to the information about the pupil acquired by the acquisition unit
wherein, if the information about the pupil indicates a second depth of focus greater than a first depth of focus, increasing the moving distance of the fixation target image or the number of times of movement of the fixation target image as compared to the moving distance or the number of times of movement of the fixation target image when the information about the pupil indicates the first depth of focus.

10. A non-transitory computer-readable storage medium storing a program that causes a computer to execute the method according to claim 9.

\* \* \* \* \*